(12) United States Patent
Liang et al.

(10) Patent No.: US 10,105,113 B2
(45) Date of Patent: Oct. 23, 2018

(54) ROTATING-GRATING CONE BEAM CT

(71) Applicants: Yueqiang Liang, Suzhou (CN);
Baosheng Li, Jinan (CN)

(72) Inventors: Yueqiang Liang, Suzhou (CN);
Baosheng Li, Jinan (CN)

( * ) Notice: Subject to any disclaimer, the term of this patent is extended or adjusted under 35 U.S.C. 154(b) by 377 days.

(21) Appl. No.: 15/017,631

(22) Filed: Feb. 7, 2016

(65) Prior Publication Data

US 2016/0151028 A1    Jun. 2, 2016

Related U.S. Application Data

(63) Continuation of application No. PCT/CN2014/085759, filed on Sep. 2, 2014.

(30) Foreign Application Priority Data

Sep. 11, 2013   (CN) .......................... 2013 1 0411677

(51) Int. Cl.
*A61B 6/00*    (2006.01)
*A61B 6/03*    (2006.01)

(52) U.S. Cl.
CPC ............ *A61B 6/4035* (2013.01); *A61B 6/035* (2013.01); *A61B 6/4085* (2013.01);
(Continued)

(58) Field of Classification Search
CPC ... A61B 6/4035; A61B 6/4085; A61B 6/5205; A61B 6/032; A61B 6/035; A61B 6/4078; A61B 6/4441; A61B 6/547; A61B 6/5282
See application file for complete search history.

(56) References Cited

U.S. PATENT DOCUMENTS

| | | | | |
|---|---|---|---|---|
| 4,132,895 A | * | 1/1979 | Froggatt | .................. A61B 6/06 378/11 |
| 5,214,686 A | * | 5/1993 | Webber | .................... A61B 6/14 378/147 |

(Continued)

*Primary Examiner* — Chih-Cheng Kao
(74) *Attorney, Agent, or Firm* — Wayne & Ken, LLC; Tony Hom

(57) ABSTRACT

Disclosed is a rotating-grating cone beam CT imaging apparatus. This imaging apparatus is composed of a frame, a frame angle sensor, an X-ray source equipped with a rotating grating, a flat panel detector, a main controller and an image reconstruction workstation. Like a general cone beam CT imaging apparatus, this imaging apparatus also adopts an open structure. But unlike the general cone beam CT imaging apparatus, the rotating grating limits X-rays emitted from the X-ray source to a plurality of narrow-angle cone beams or sector beams. In the process that the X-ray source and the detector rotate around an imaging object, projection images of the narrow-angle cone beams or sector beams on the flat panel detector move back and forth continually through the rotation of the rotating grating, so as to acquire projection information about the imaging object in an entire scanning region. Finally, the projection information is reconstructed into a volume image in the image reconstruction workstation. In this manner of variable-focus scanning, the present invention not only can reserve the advantage of the open structure of the cone beam CT imaging apparatus, but also obtains the advantage that a sector beam CT imaging apparatus can restrain scattered photons so as to generate a high-quality image.

7 Claims, 3 Drawing Sheets

(52) U.S. Cl.
CPC .......... *A61B 6/5205* (2013.01); *A61B 6/5282* (2013.01); *A61B 6/547* (2013.01); *A61B 6/032* (2013.01); *A61B 6/4078* (2013.01); *A61B 6/4441* (2013.01)

(56) References Cited

U.S. PATENT DOCUMENTS

| | | | | |
|---|---|---|---|---|
| 6,229,870 B1* | 5/2001 | Morgan | ............... | A61B 6/032 378/4 |
| 2006/0002506 A1* | 1/2006 | Pelc | ............... | A61B 6/032 378/12 |
| 2007/0280408 A1* | 12/2007 | Zhang | ............... | A61B 6/025 378/10 |

* cited by examiner

ROTATING-GRATING CONE BEAM CT

CROSS-REFERENCE TO RELATED APPLICATIONS

This application is a continuation of International Patent Application No. PCT/CN2014/085759 with an international filing date of Sep. 2, 2014 designating the United States, and further claims priority benefits to Chinese Patent Application No. 201310411677.X filed Sep. 11, 2013. The content of the aforementioned applications, including any intervening amendments thereto, is incorporated herein by reference.

TECHNICAL FIELD

The present invention relates to the field of X-ray imaging apparatus, more particularly, to a rotating-grating cone beam CT

BACKGROUND

At present, the cone beam CT has been widely applied to stomatology and tumor radiotherapy already, which has the advantages of open structure and convenience in use, but compared with the sector beam CT, the cone beam CT has the disadvantage of inaccurate image density information.

When projection images are acquired by the cone beam CT, scattered photons influence the projection images, which is the main reason why the image density of the sector beam CT is inaccurate. At present, there are mainly two kinds of methods to reduce the influence of the scattered photons. One kind is a physical method. For example, a beam limitation device is adopted to limit the range of cone beams. Since the smaller the cone angle of the cone beam CT is, the fewer the components of the scattered photons in the projection images are, but while the range of the cone beams is limited, the imaging range is also limited. This method cannot be applicable to a larger imaging object. The other physical method is to add a backscattering grid between the imaging object and the flat panel detector. Although the backscattering grid can restrain the scattered photons in the projection images, noise may be introduced. This method has a better effect for the situation where the distance between the imaging object and the detector is smaller, but for the situation where the distance between the imaging object and the detector is larger, such as the cone beam CT which is integrated into an accelerator and is used in the image-guided radiotherapy, the effect of adding the backscattering grid is limited. The other kind is a method of postprocessing after collection of projection images. For example, a monte carlo algorithm is adopted, so that the distribution of the scattered photons in the projection images can be estimated accurately. Therefore, the influence of the scattered photons is eliminated from the projection images. However, even some simplified calculation technologies are adopted, the monte carlo algorithm has overlarge amount of calculation, and thus the scattering distribution with high resolution cannot generate within the time of clinical acceptability. The distribution of the scattered photons is calculated using an analytical model. Although the calculation speed is faster, for a complex imaging objective, a larger calculation deviation may be generated. For another example, a noise suppression reconstruction algorithm is adopted, and the scattered photons in the projection images are regarded as noise during image reconstruction, so that the influence of the scattered photons can also be reduced to a certain extent.

The above-mentioned technologies have effect of reducing the influence of the scattered photons, but also have limitations. At present, the accuracy of the reconstructed image density of the cone beam CT is still obviously lower than that of the traditional sector beam CT.

In consideration that the smaller the cone angle of the cone beam CT is, the fewer the components of the scattered photons in the projection images are, a rotating-grating cone beam CT imaging apparatus is invented. A grating limits X-rays emitted from the X-ray source to a plurality of narrow-angle cone beams or sector beams, and then the positions of the narrow-angle cone beams or sector beams are changed through the rotation of the grating, so that projection images of different regions of the imaging object are acquired, thereby greatly reducing the influence of the scattered photons on the image quality.

SUMMARY OF THE INVENTION

Under the elicitation of a sector beam CT, in consideration that the smaller the beams are (or the narrower the beams are), the fewer the components of the scattered photons are, a rotating-grating cone beam CT imaging apparatus is invented.

This imaging apparatus is composed of a frame and a drive device thereof, a frame angle sensor, an X-ray source equipped with a rotating grating, a flat panel detector, a main controller and an image reconstruction workstation. The frame drive device drives the frame to rotate around an imaging object in the process of image collection. The X-ray source equipped with the rotating grating and the flat panel detector are mounted on the frame, and can rotate together with the frame. The X-ray source equipped with the rotating grating is composed of an X-ray source, a rotating grating drive device, a grating angle sensor and a rotating grating. The rotating grating limits X-rays emitted from the X-ray source to a plurality of narrow-angle cone beams or sector beams. Slits of the gratings located at different rotation angles have different positions, so that when the rotating grating rotates, the positions of the narrow-angle cone beams or sector beams passing through the gratings can be changed. In the process of collecting projection images, while the X-ray source equipped with the rotating grating rotate together with the frame, the rotating grating also rotates around the X-ray source, so that the projection images of the narrow-angle cone beams or sector beams passing through the gratings scan the entire flat panel detector, so as to acquire projection information about an entire volume image. In this way, the projection images are obtained in the manner that a plurality of narrow-angle cone beams scan back and forth continually instead of the manner of projecting a cone beam. The narrow-angle cone beams enable more scattered rays to be removed, thereby reducing the influence of scattered photons on the projection images, so that a CT image having high definition is reconstructed.

The rotating grating angle sensor detects the rotation angle of the gratings in real time, and transmits this angle information to the main controller. The main controller is used for synchronizing the rotation of the gratings and the image collection of the flat panel detector.

The frame angle sensor detects the rotation angle of the frame in real time, and transmits this angle information to the main controller. The main controller records the frame angle during collection of each projection image.

The portions of the acquired projection images which are covered by the gratings are regarded as scattering signals, and the portions thereof which are not covered by the gratings are regarded as the superposition of main X-ray signals and scattering signals. The scattering signals of the portions which are not covered by the gratings can be estimated through the scattering signals of the portions which are covered by the gratings using an interpolation algorithm, such as a cubic spline interpolation algorithm. In this way, the main X-ray projection signals can be obtained by subtracting the estimated scattering signals from the projection signals of the portions which are not covered by the gratings.

The image reconstruction workstation reconstructs a three-dimensional volume image using these main X-ray projection signals and the corresponding frame angles acquired from the main controller, and adopting an FDK reconstruction algorithm, a compressive sensing reconstruction algorithm or an iterative optimization reconstruction algorithm.

This imaging apparatus not only uses the advantage that the narrow-angle cone beams or sector beams can restrain the scattered photons so as to generate a high-quality image, but also obtains the open structure of the cone beam CT imaging apparatus in the manner of rotating the gratings.

DETAILED DESCRIPTION

Specific Embodiment 1

Figure 1:
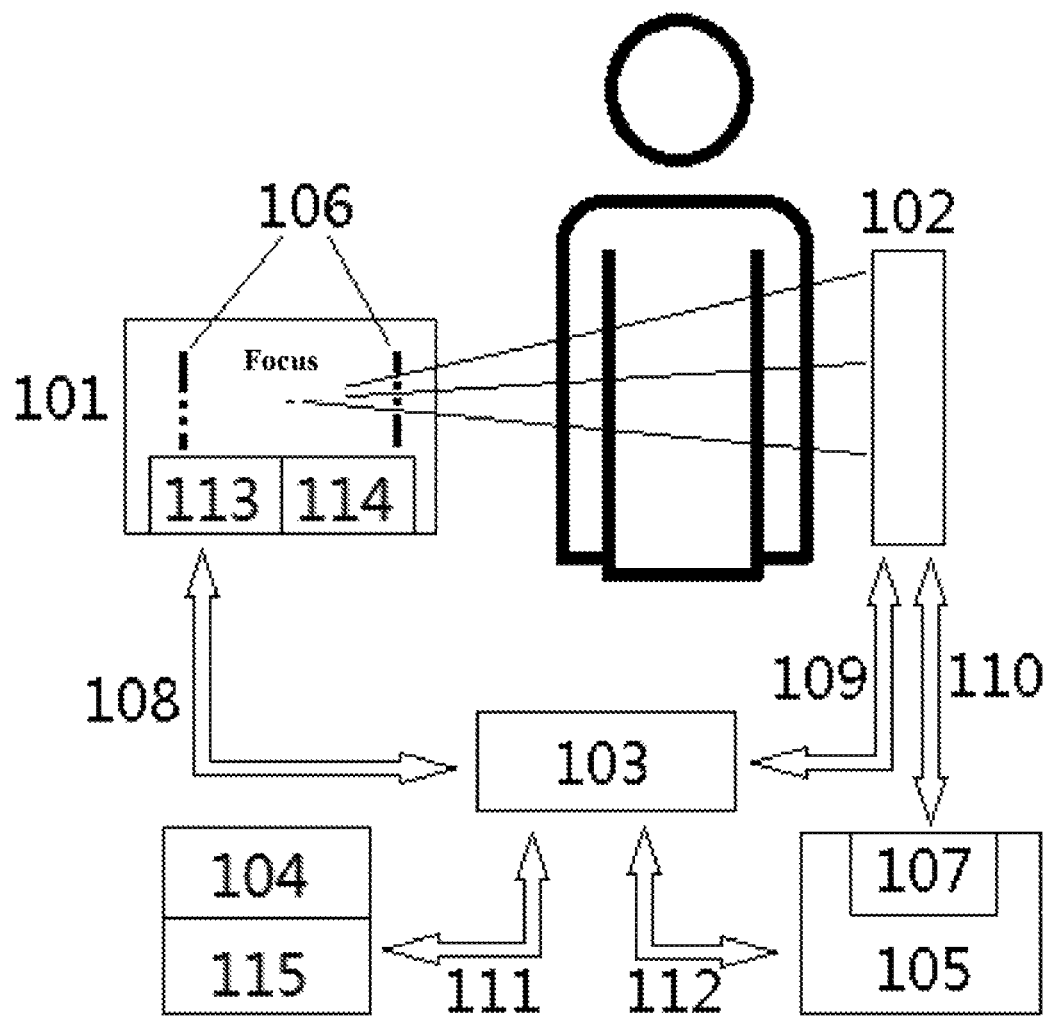
FIG. 1 is a schematic diagram of data communication between portions in embodiment 1.

FIG. 1 shows an embodiment of a rotating-grating cone beam CT imaging apparatus.

In FIG. 1, 101 is an X-ray source with a rotating grating, and when the grating rotates, the positions of X-ray beams passing through the gratings can be changed, wherein 106 is a rotating grating made of tungsten alloy material, 113 is a grating angle sensor, and 114 is a rotating grating drive device. The rotating grating limits X-rays generated in the X-ray source to a plurality of narrow-angle cone beams. In FIG. 1, 102 is a flat panel detector, 105 is an image reconstruction workstation, and 107 is an image collection card mounted on the image reconstruction workstation.

In FIG. 1, 103 is a main controller. The main controller drives the frame and the gratings to rotate through the frame drive device and the rotating grating drive device. The main controller acquires angle signals of the frame and the gratings through the frame angle sensor 104 and the grating angle sensor 113. The main controller is also used for synchronizing the beam emission of the X-ray source, the rotation of the gratings and the projection signal collection of the flat panel detector. The working process thereof has the following steps:

a) the image reconstruction workstation sends an image collection start command to the main controller;

b) the main controller drives the gratings to rotate at an angular speed of 6 r/s through the rotating grating drive device;

c) the main controller drives the frame to rotate at an angular speed of 6 rad/s through the frame drive device;

d) the main controller detects the rotation of the gratings through the grating angle sensor, sends a control signal to the flat panel detector when a new group of gratings enters between the X-ray source and the imaging object, and removes image data of the flat panel detector;

e) the main controller sends a control signal to the X-ray source to enable the X-ray source to emit beams;

f) from the frame angle sensor, the main controller reads a frame angle when the exposure starts;

g) after the designated exposure time is over, the image reconstruction workstation reads the image data of the flat panel detector through the image collection card;

h) the main controller sends a control signal to the X-ray source to enable the X-ray source to stop emitting beams;

i) the main controller reads a frame angle when the exposure ends; and j) return to step d) again, and repeat continually in the sequence of step d), e), f), g), h) and i) until the frame completes the rotation at 360°.

The image reconstruction workstation firstly preprocesses projection images read from the detector, estimates scattering signals of portions which are not covered by the gratings using scattering signals of portions which are covered by the gratings through a cubic spline interpolation algorithm, and removes these estimated scattering signals from the projection images of the portions which are not covered by the gratings.

Finally, the image reconstruction workstation reconstructs a three-dimensional volume image using the projection images from which the scattering signals have been removed, and frame angles which are acquired from the main controller and correspond to these projection images, and adopting a compressive sensing reconstruction algorithm.

In FIG. 1, a signal 108 is a control signal which is sent to the X-ray source with the rotating grating by the main controller, and a response; a signal 109 is a control signal which is sent to the flat panel detector by the main controller, and a response; a signal 110 is a control signal which is sent to the flat panel detector by the image reconstruction workstation, and a read projection image; a signal 111 is a control signal which is sent to the frame drive device by the main controller, and a frame angle which is sent to the main controller by the frame angle sensor; and a signal 112 is a control signal which is sent to the main controller by the image reconstruction workstation, and information, such as a returned frame angle corresponding to each projection image, etc.

Figure 2:
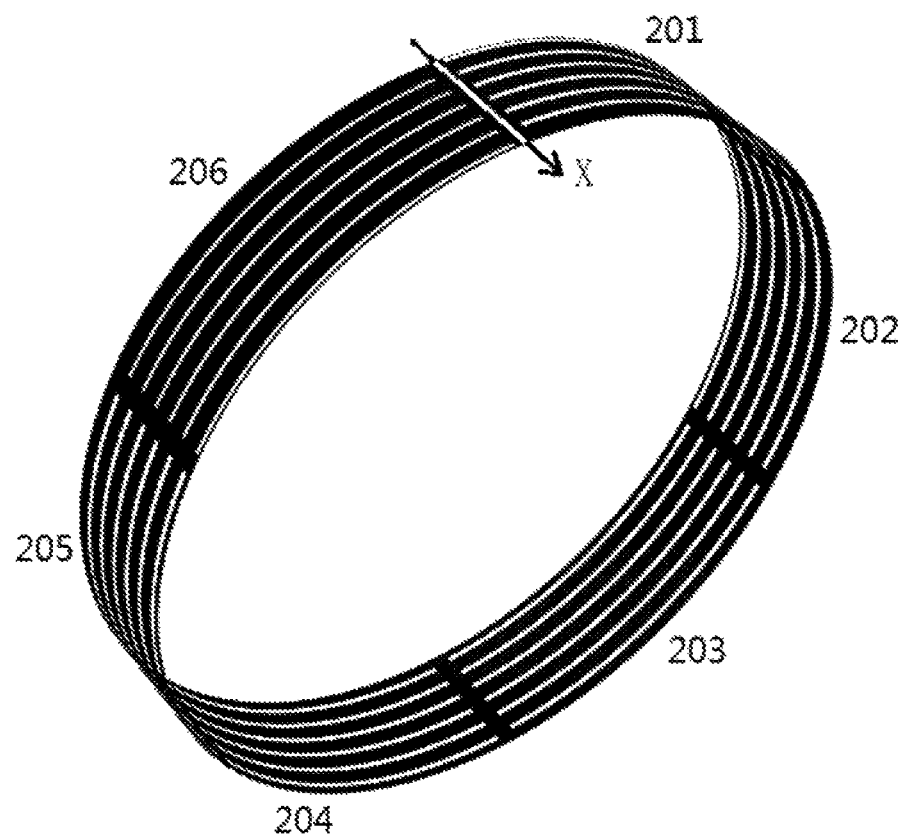
FIG. 2 is a diagram of a rotating grating in embodiment 1.

FIG. 2 shows the rotating grating in embodiment 1. Gratings are made of tungsten alloy material. A group of gratings exists at intervals of 60°, and there are 6 groups of gratings in total in the sequence of 201, 202, 203, 204, 205 and 206. Each group of gratings is composed of 6 slits, each slit is 3 mm in width, and the center-to-center spacing between every two adjacent slits in the same group is 12 mm. Starting from 201, as compared with the slits of the previous group of gratings, the slits of the next group of gratings offset for 2 mm in the X positive direction in the figure entirely.

Figure 3:
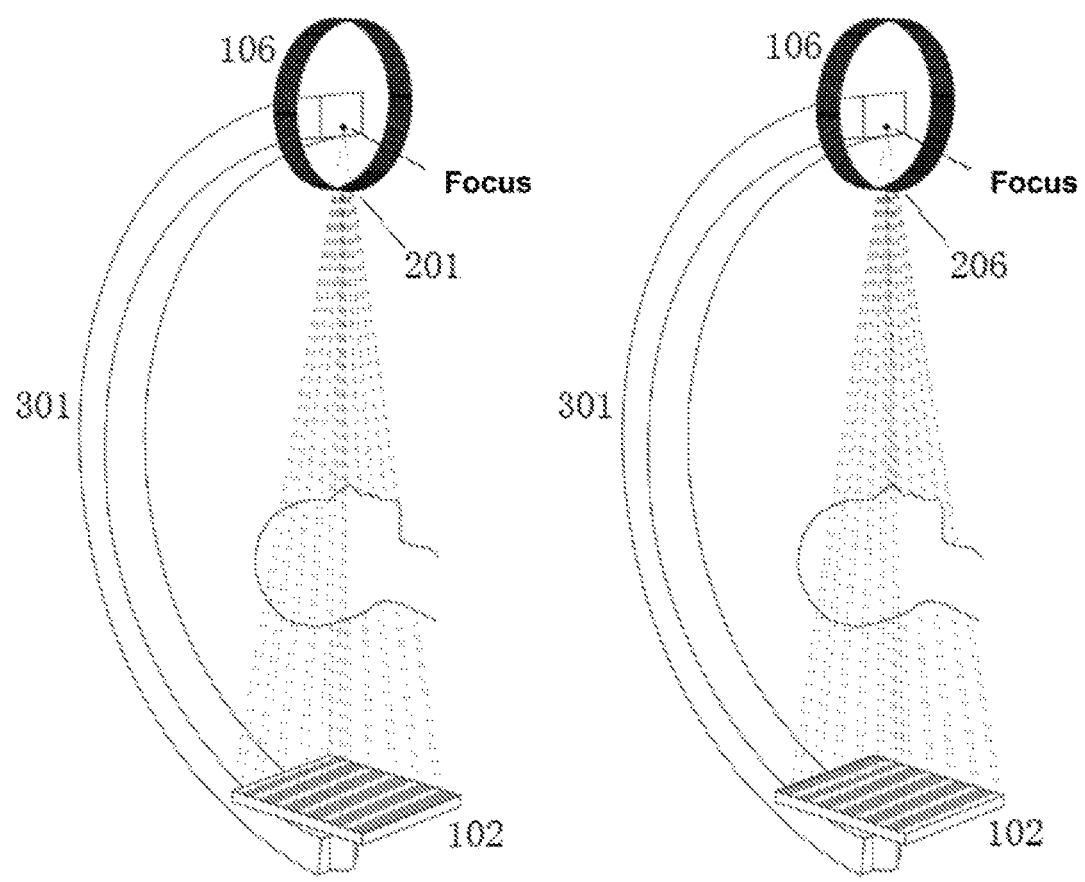
FIG. 3 is a schematic diagram of operation of the rotating grating in embodiment 1.

FIG. 3 shows a schematic diagram of operation of the rotating grating in embodiment 1. In FIG. 3, 301 is a C-arm frame. 106 is a rotating grating, 102 is a flat panel detector, 201 is the $1^{st}$ group of gratings in the rotating grating, and 206 is the $6^{th}$ group of gratings in the rotating grating. The X-ray source with the rotating grating and the flat panel detector are both mounted on the frame, and rotate around the imaging object together with the frame when the projection images are collected. The rotating grating limits the X-rays emitted from the X-ray source to a plurality of narrow-angle cone beams (as shown by the dotted lines in the figure). In the left figure of FIG. 3, the 1$^{st}$ group of gratings 201 in the rotating grating is located between a focus and the imaging object, the rays emitted from the X-ray source pass through the gratings, so that a group of bar regions slightly on the left of the flat panel detector is exposed. In the process of rotation of the gratings, the positions of the exposed regions are switched continually from left to right, and the projection images are returned to the image reconstruction workstation. Until the 6$^{th}$ group of gratings 206 in the rotating grating rotates between the focus and the imaging object, as shown in the right figure of FIG. 3, the rays emitted from the X-ray source pass through the gratings, so that a group of bar regions slightly on the right of the flat panel detector is exposed, thereby completing scanning the imaging object completely once. In the process that the frame rotates at 360°, the rotating grating needs to rotate 360 r, that is, the imaging object is scanned 360 times in the above-mentioned manner from left to right, so as to obtain adequate reconstruction information.

We claim:

1. A rotating-grating cone beam CT imaging apparatus, characterized in that said apparatus is composed of a frame and a drive device thereof, a frame angle sensor, an X-ray source equipped with a rotating grating, a flat panel detector, a main controller and an image reconstruction workstation,
   wherein said X-ray source is mounted on the frame, and rotates together with the frame in the process of collecting projection images, and while the X-ray source rotates together with the frame, said rotating grating also rotates around the X-ray source, so that projection images of narrow-angle cone beams or sector beams passing through the rotating grating scan the entire flat panel detector, and this scanning process is repeated continually;
   and said rotating grating is composed of several groups of gratings located at different rotation angles, said several groups of gratings extend and are distributed in length in the circumferential direction of said rotating grating, and as compared with the slits of the previous group of gratings in said several groups of gratings, the slits of the next group of gratings axially offset along said rotating grating entirely, so that when said rotating grating rotates, the positions of the narrow-angle cone beams or sector beams passing through the gratings can be changed.

2. The rotating-grating cone beam CT imaging apparatus of claim 1, characterized in that said frame drive device drives the frame to rotate around an imaging object in the process of image collection.

3. The rotating-grating cone beam CT imaging apparatus of claim 1, characterized in that said rotating grating rotates around the X-ray source in the process of image collection.

4. The rotating-grating cone beam CT imaging apparatus of claim 1, characterized in that said rotating grating limits X-rays emitted from the X-ray source to a plurality of narrow-angle cone beams or sector beams.

5. The rotating-grating cone beam CT imaging apparatus of claim 1, characterized in that said flat panel detector is mounted on the frame, and rotates together with the frame in the process of collecting projection images.

6. The rotating-grating cone beam CT imaging apparatus of claim 1, characterized in that said image reconstruction workstation estimates the distribution of scattering signals in the portions of the narrow-angle cone beams or the sector beams using the projection signals of the portions in the projection images which are covered by the gratings, the projection signal being read from the detector; and removes the estimated scattering signals from the projection images.

7. The rotating-grating cone beam CT imaging apparatus of claim 6, characterized in that said image reconstruction workstation reconstructs a three-dimensional volume image using the projection images from which the scattering signals have been removed, and rotating grating angles and frame angles which are acquired from the main controller and correspond to these projection images, and adopting an FDK reconstruction algorithm, a compressive sensing reconstruction algorithm or an iterative optimization reconstruction algorithm.

* * * * *